United States Patent
Pigott

(10) Patent No.: US 10,130,798 B2
(45) Date of Patent: Nov. 20, 2018

(54) BALLOON CATHETER HAVING A RETRACTABLE SHEATH AND LOCKING MECHANISM

(71) Applicant: John P. Pigott, Sylvania, OH (US)

(72) Inventor: John P. Pigott, Sylvania, OH (US)

(*) Notice: Subject to any disclaimer, the term of this patent is extended or adjusted under 35 U.S.C. 154(b) by 133 days.

(21) Appl. No.: 14/990,477

(22) Filed: Jan. 7, 2016

(65) Prior Publication Data

US 2016/0166810 A1   Jun. 16, 2016

Related U.S. Application Data

(63) Continuation of application No. PCT/US2014/046616, filed on Jul. 15, 2014.

(60) Provisional application No. 62/102,770, filed on Jan. 13, 2015, provisional application No. 62/012,382, filed on Jun. 15, 2014, provisional application No. 61/846,095, filed on Jul. 15, 2013.

(51) Int. Cl.
   *A61M 31/00* (2006.01)
   *A61M 37/00* (2006.01)
   *A61M 25/10* (2013.01)

(52) U.S. Cl.
   CPC ..... *A61M 25/10* (2013.01); *A61M 2025/1068* (2013.01); *A61M 2025/1081* (2013.01)

(58) Field of Classification Search
   CPC .. A61M 2025/1068; A61M 2025/1081; A61M 25/10; A61M 2025/0046; A61M 2025/1079; A61M 25/0045
   See application file for complete search history.

(56) References Cited

U.S. PATENT DOCUMENTS

| | | | |
|---|---|---|---|
| 4,292,974 A | 10/1981 | Fogarty et al. | |
| 5,246,421 A | 9/1993 | Saab | |
| 5,514,093 A | 5/1996 | Ellis et al. | |
| 5,591,194 A | 1/1997 | Berthiaume | |
| 5,658,309 A | 8/1997 | Berthiaume et al. | |
| 5,676,654 A | 10/1997 | Ellis et al. | |
| 5,697,948 A | 12/1997 | Marin et al. | |
| 5,961,536 A | 10/1999 | Mickley et al. | |
| 6,071,287 A * | 6/2000 | Verbeek | A61F 2/95 604/96.01 |
| 6,270,489 B1 * | 8/2001 | Wise | A61M 25/003 604/508 |
| 6,695,863 B1 | 2/2004 | Ramzipoor et al. | |
| 6,719,773 B1 | 4/2004 | Boucher et al. | |
| 6,884,257 B1 * | 4/2005 | Cox | A61F 2/958 604/103.05 |
| 8,500,789 B2 | 8/2013 | Wuebbeling et al. | |
| 2004/0267345 A1 | 12/2004 | Lorenzo et al. | |
| 2005/0055077 A1 | 3/2005 | Marco et al. | |

(Continued)

FOREIGN PATENT DOCUMENTS

| WO | 8102109 A1 | 8/1981 |
|---|---|---|
| WO | 2007095125 A2 | 8/2007 |
| WO | 2014106226 A2 | 7/2014 |

*Primary Examiner* — Rebecca E Eisenberg
(74) *Attorney, Agent, or Firm* — Standley Law Group LLP

(57) ABSTRACT

An intravascular balloon catheter device is disclosed having an inner member, an outer member disposed about the inner member and further comprising a balloon. A sheath is disposed about the outer member that moves relative to the balloon so as to selectively expose some or all of the balloon for inflation. A clamp may be used to selectively secure the sheath at a desired position relative to the balloon.

11 Claims, 17 Drawing Sheets

(56) References Cited

U.S. PATENT DOCUMENTS

| | | |
|---|---|---|
| 2005/0151304 A1 | 7/2005 | Boelens et al. |
| 2008/0140051 A1 | 6/2008 | Bei et al. |
| 2009/0105686 A1 | 4/2009 | Snow et al. |
| 2012/0143054 A1 | 6/2012 | Eaton et al. |
| 2013/0237950 A1 | 9/2013 | Gianotti et al. |
| 2013/0253467 A1 | 9/2013 | Gianotti et al. |

* cited by examiner

FIG—9

BALLOON CATHETER HAVING A RETRACTABLE SHEATH AND LOCKING MECHANISM

CROSS-REFERENCE TO RELATED APPLICATION

This application claims the benefit of U.S. Provisional Application No. 62/102,770, filed Jan. 13, 2015, the disclosure of which is incorporated herein by reference. Additionally, this application is a continuation of International Application No. PCT/US2014/046616, filed Jul. 15, 2014, which claims the benefit of U.S. Provisional Application No. 62/012,382, filed Jun. 15, 2014 and U.S. Provisional Application 61/846,095, filed Jul. 15, 2013, the disclosures of which are incorporated herein by reference.

TECHNICAL FIELD

Exemplary embodiments of the present invention generally relate to balloon catheters used in surgical procedures.

BACKGROUND AND SUMMARY OF THE INVENTION

This invention relates in general to balloon catheters that are used in surgical procedures. In particular, this invention relates to an improved structure for such a balloon catheter having a retractable sheath that can quickly and easily adjust the length of the inflated portion of the balloon and a locking mechanism for selectively retaining the sheath in the desired position for use.

In many surgical procedures, such as but not limited to percutaneous transluminal angioplasty procedures, a catheter having a selectively inflatable portion provided thereon (commonly referred to as a balloon catheter) is used to open a blockage and/or place a stent in a blood vessel. To accomplish this, a user st select one of various sized balloons to match the blood vessel structure and the length of the treatment area. The balloon of the catheter is initially positioned at a desired zone of attention within the blood vessel. Then, the balloon of the catheter is inflated so as to expand into engagement with an inner surface of the blood vessel, thereby expanding the blockage. If desired, an expandable stent can be disposed about the balloon of the catheter such that when the balloon is inflated, the stent is expanded into engagement with the inner surface of the blood vessel. The balloon and/or the stent is often treated with medication that is delivered by contact with the surface of the blood vessel when the balloon and/or stent is deployed. In either event, the balloon is subsequently deflated after use.

It is important that the balloon be properly sized to the treatment area. If a balloon catheter is too long, the balloon may damage the surrounding tissue. If a balloon is too short, the treatment may be ineffective or require time-consuming repetition. Therefore, care facilities are forced to stock many different size balloon catheters and medical care providers must spend time carefully selecting the properly sized balloon catheter. What is needed is a variable length balloon catheter. Therefore, it would be desirable to provide an improved structure for such a balloon catheter having a retractable sheath that can quickly and easily adjust the length of the portion of the balloon to be inflated and a locking mechanism for selectively retaining said sheath in the desired position for use.

Due to internal pressure, shape, and texture, a partially exposed balloon catheter would have a natural tendency to escape the retractable sheath when inflated. This is much like how a partially protruding watermelon seed has a natural tendency to entirely escape a person's lips, due to the watermelon seed's shape and texture. Here, the same phenomenon applies to a partially exposed balloon catheter from a sheath, though the situation is further complicated by the internal pressure of the balloon. Therefore, it would be desirable to additionally provide a mechanical stop in conjunction with the device where said mechanical stop serves to prevent the balloon from entirely escaping the retractable sheath when the balloon is inflated. Further, the mechanical stop can be used to adjust the effective area of the balloon catheter by controlling the length of the balloon permitted to extend from the sheath.

Recently, medical practitioners have realized that drug coatings may be applied to the outer surface of the intravascular balloons to increase the effectiveness of medical treatment. These so called "drug coated balloons" are exposed to blood and other intravascular fluids upon being inserted into a person's vascular system. This may result in the premature activation, elution, dilution, and loss of the drug coating on the way to the treatment zone. Therefore, it would be desirable to provide a watertight seal between the balloon and the sheath such that the medicated balloon is not exposed to intravascular fluids until the balloon reaches the treatment zone.

The present invention is directed to an improved structure for a balloon catheter having a retractable sheath that can quickly and easily adjust the length of the inflated portion of the balloon and a locking mechanism for selectively retaining the sheath in the desired position for use. The balloon catheter assembly includes an inner member and an outer member that is disposed about the inner member. The outer member includes an inflatable balloon. A sheath is disposed about the outer member for movement relative to the balloon so as to selectively expose some or all of the balloon for inflation. The balloon catheter assembly includes a clamp for selectively securing the sheath at a desired position relative to the balloon. The inner member may comprise a series of indentations or protrusion that engage the clamp such that the user may selectively control the location of the retractable sheath relative to the balloon.

The assembly may further include a mechanical stop that is configured to selectively secure the balloon and prevents it from entirely escaping the sheath when the balloon is inflated. The assembly may comprise a series of graduated markers, such as radiopaque markers, that indicate the position of the balloon relative to the retractable sheath. The balloon may further comprise a strength collar, such as an annulus, located on the distal end of the retractable sheath.

Additionally, the balloon and the sheath may form a substantially watertight engagement with one another. This seal may prevent the medicated coating from being prematurely removed, eluted, or activated prior to the assembly being properly located at the treatment site. In exemplary embodiments of the present invention, the assembly may further comprise a cap that provides a substantially watertight engagement between said cap and the sheath when the balloon is in a retracted position such that the cap abuts the sheath. The balloon may further comprise a lubricious coating between the outer surface of the balloon and the inner surface of the sheath which allows the balloon to move relative to the sheath without disturbing the medicated coating.

Various aspects of this invention will become apparent to those skilled in the art from the following detailed description of the preferred embodiments, when read in light of the accompanying drawings.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Figure 1:
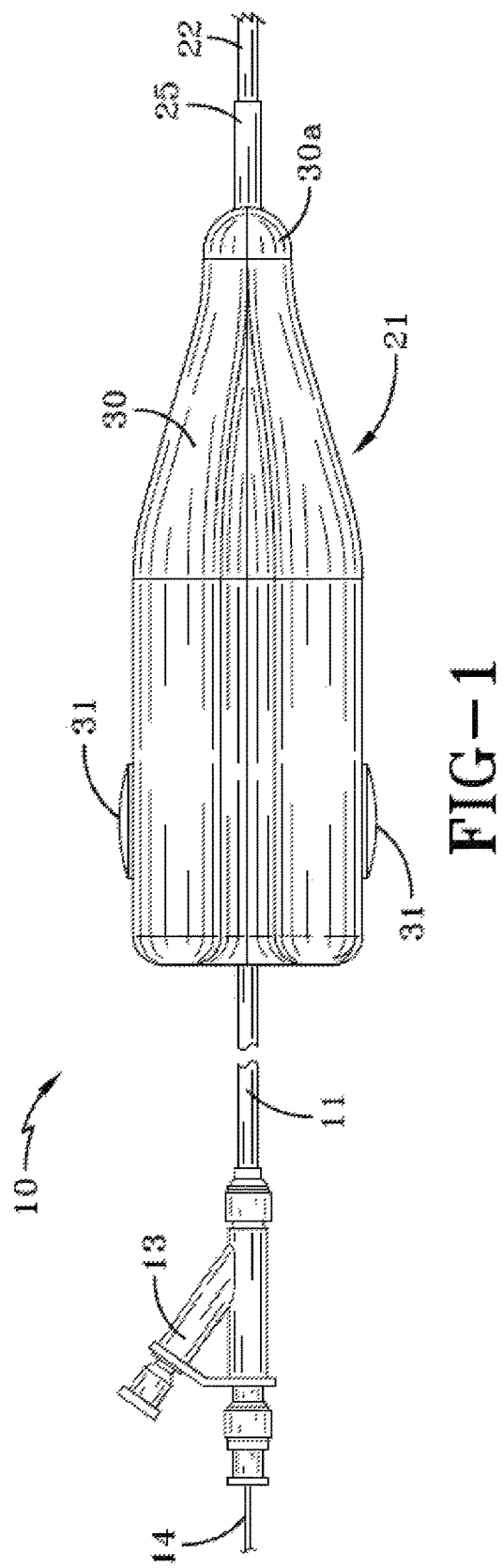
FIG. 1 is a side elevation view of a first end of a balloon catheter assembly.

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 2:
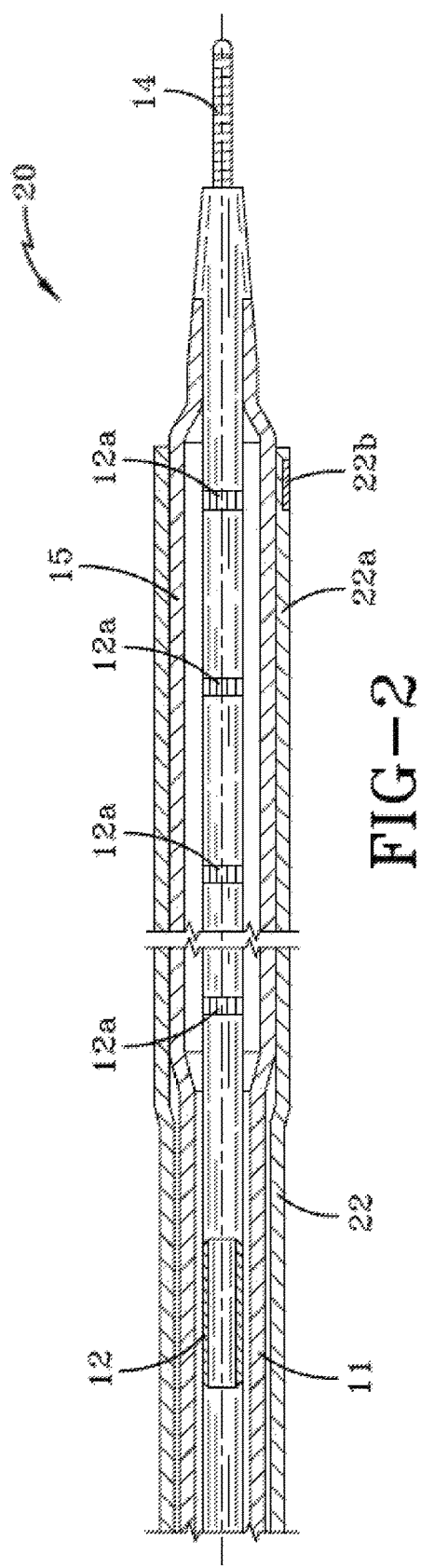
FIG. 2 is an enlarged sectional elevation view of a second end of the balloon catheter assembly illustrated in FIG. 1.

FIG. 1 and FIG. 2 illustrate a balloon catheter assembly, indicated generally at 10. The balloon catheter assembly is comprised of a first end, illustrated in FIG. 1, and a second end, illustrated in FIG. 2. The balloon catheter assembly 10 has an elongated shaft portion that includes an outer member 11 and an inner member 12. The outer member 11 and the inner member 12 may both be tubular in shape, although such is not required. The inner member 12 is disposed within the outer member 11. Thus, an annular outer lumen is defined between the inner surface of the outer tubular member 11 and the outer surface of the inner tubular member 12. Similarly, a cylindrical inner lumen is defined within the inner tubular member 12. The purpose for the outer and inner lumens will be explained below.

In exemplary embodiments of the present invention, one or more radiopaque markers 12a may be provided on the inner tubular member 12. The radiopaque markers 12a are conventional in the art and are provided to facilitate the determination of the location of the inner tubular member 12 during a procedure using conventional fluoroscopy techniques. The radiopaque markers 12a may be spaced in regular intervals. Further, one or more radiopaque markers 22b may be provided on the expanded portion 22a of the sheath 22 to facilitate the determination of the location of the sheath 22 using conventional fluoroscopy techniques during use. The radiopaque markers 12a and 22b may be monitored by the user to determine how far the inner member 12a, and thus the balloon 15, is extended from the sheath 22 thereby permitting the user to monitor how much of the balloon 15 is exposed for treatment of the affected area.

An adapter 13 may be connected to a first end of the elongated shaft portion of the balloon catheter assembly 10. The adapter 13 is conventional in the art and is provided to facilitate access to both the outer and inner lumens during use of the balloon catheter assembly 10. For example, a guide wire 14 can be inserted into the inner lumen via the adapter 13 and through a second end of the elongated shaft portion of the balloon catheter assembly 10, as shown in FIG. 2. The guide wire 14 is conventional in the art and is provided to facilitate the positioning of the balloon catheter assembly 10 at a desired location for use, such as within a blood vessel as described above.

The outer tubular member 11 includes an inflatable balloon 15. The balloon 15 is conventional in the art and may be connected to the outer tubular member 11 such that at least a portion of the inflatable balloon 15 extends about an end portion of the inner tubular member 12. The interior of the balloon 15 communicates with the outer lumen of the balloon catheter assembly 10. As a result, an inflation fluid can be selectively introduced into the adapter 13 and through the outer lumen to the interior of the balloon 15, causing it to inflate in a known manner. Additionally, the interior of the balloon 15 can be vented through the outer lumen and the adapter 13 to the atmosphere, allowing it to deflate after use.

The balloon catheter assembly 10 includes an adjustable sheath assembly, indicated generally at 20. As will be explained in detail below, the adjustable sheath assembly 20 is provided to selectively define a portion of the balloon 15 that is desired to be inflated during use. To accomplish this, the balloon catheter assembly 10 includes a clamp, indicated generally at 21, and a sheath 22. The clamp 21 is disposed about the outer member 11 adjacent to the adapter 13 and the first end of the elongated shaft portion of the balloon catheter assembly 10. The structure and operation of the clamp 21 will be explained in detail below.

The sheath 22 may extend from the clamp 21 about the outer member 11 toward the second end of the elongated shaft portion of the balloon catheter assembly 10. In the illustrated embodiment, the sheath 22 includes an expanded portion 22a that is located adjacent to the second end of the elongated shaft portion of the balloon catheter assembly 10. One or more optional radiopaque markers 22b may be provided on the expanded portion 22a of the sheath 22 to facilitate the determination of the location of the sheath 22 using conventional fluoroscopy techniques during use. Also, the expanded portion 22a of the sheath 22 may have an elastically expandable distal tip provided thereon that is expanded in a conventional manner when the balloon 15 is inflated. The structure and operation of the optional elastically expandable distal tip will be explained in detail below.

Treatments to various size vascular zones of attention may be provided utilizing the present invention. To perform such treatments, a user may first provide an intravascular catheter device consistent with the present invention. Next, the user may direct the catheter to a pre-determined zone of attention within a person's vascular system. Then the user may move the sheath relative to the balloon so to selectively expose a portion of the balloon for inflation. The user may next temporarily secure the sheath relative to the balloon. The user may then inflate the balloon. In exemplary embodiments of the present invention, these steps may include providing a medical treatment device, such as but not limited to a stent, in conjunction with the present invention. The medical treatment device may be deployed when the balloon is inflated, or it may be deployed as another step. In either case, the balloon may then be deflated and removed.

The present invention may also provide a method for minimizing or all together eliminating premature activation, elution, dilution, or removal of a drug coating on the balloon and the medical treatment device. To do so, first the user may provide an intravascular catheter device consistent with the present invention. Next, the user may direct the catheter to the pre-determined zone of attention within the person's vascular system. Then the user may move the sheath relative to the balloon so to selectively expose a portion of the drug coated balloon or the medical treatment device for activation. The balloon may be inflated to place the outer surface of the balloon and the medical treatment device in contact with the surrounding blood vessel wall. The balloon may be deflated and removed. It is notable that while the aforementioned method is described with the medical treatment device, such is not required.

Figure 3:
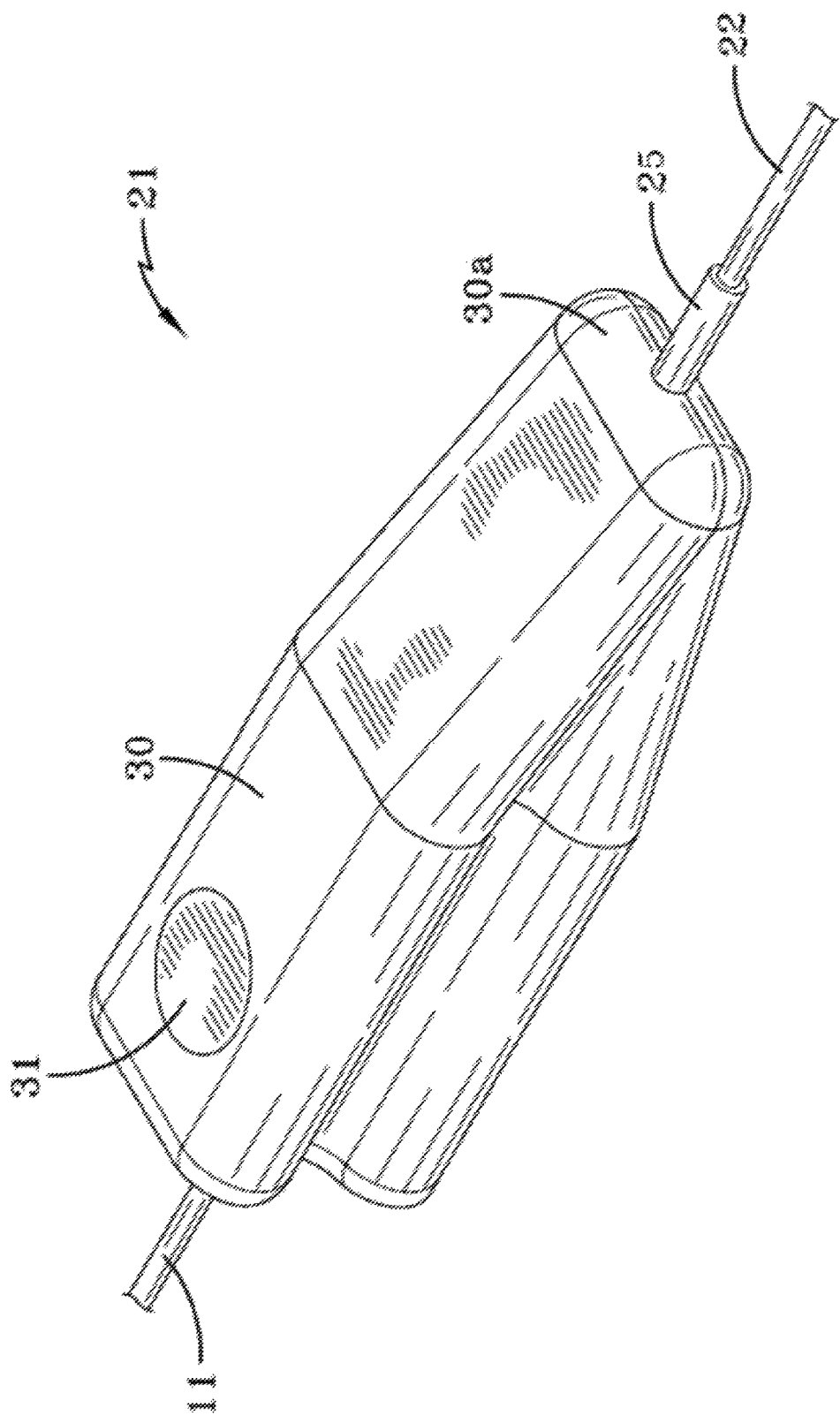
FIG. 3 is a perspective view of a clamp of the balloon catheter assembly illustrated in FIG. 1.

FIG. 3 illustrates the external structure of an exemplary embodiment of the clamp 21. As further illustrated in FIG. 4 and FIG. 5, the clamp 21 includes a housing 30 through which the outer member 11 of the elongated shaft portion of the balloon catheter assembly 10 extends. The housing 30 includes a push button 31 and a tip 30a. The tip 30a may include a protective member 25 that permits the passage of the sheath 22. In exemplary embodiments of the present invention, the sheath 22 is connected directly to the tip 30a. Thus, the housing 30 of the clamp 21 is connected to the sheath 22 for movement therewith, as will be explained in detail below.

Figure 4:
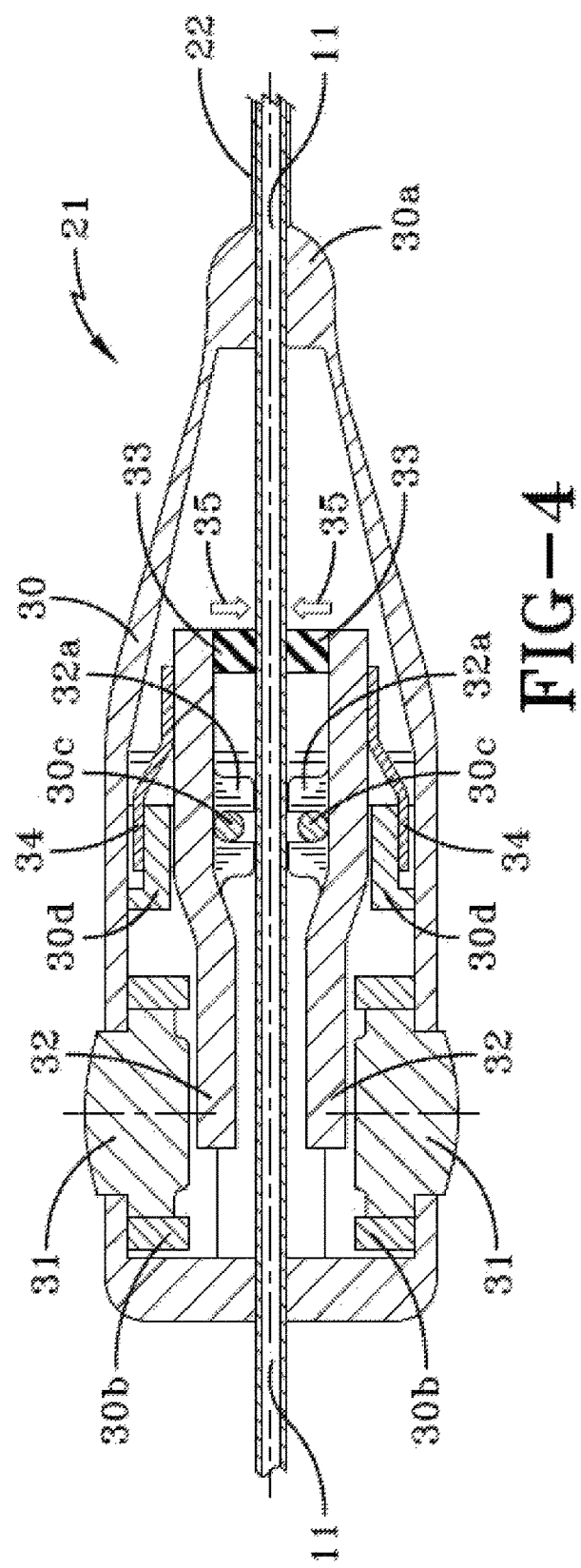
FIG. 4 is an enlarged sectional elevation view showing the clamp of the balloon catheter assembly illustrated in FIG. 1 in a locked condition.
Figure 5:
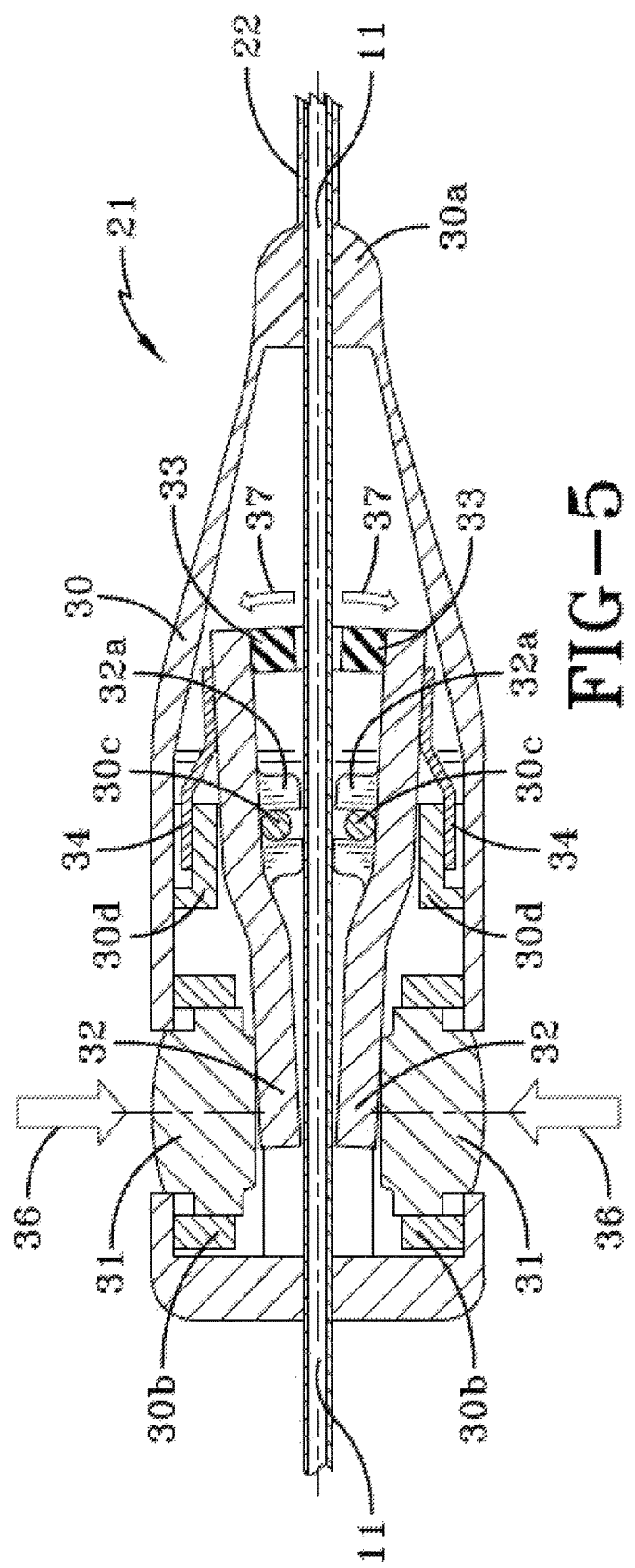
FIG. 5 is an enlarged sectional elevation view similar to FIG. 4 showing the clamp of the balloon catheter assembly in an unlocked condition.

FIG. 4 and FIG. 5 illustrate the internal structure of an embodiment of the clamp 21. The housing 30 of the clamp 21 also includes a pair of button supports 30b, within which respective manually operable push buttons 31 are supported for inward and outward movement relative to the housing 30. In the illustrated embodiment, each of the button supports 30b is generally hollow and cylindrical in shape, and each of the push buttons 31 is generally cylindrical in shape. However, the button supports 30b and the push buttons 31 may have any desired shape or combination of shapes. The purpose for the push buttons 31 will be explained below.

The housing 30 of the clamp 21 further includes a pair of actuator arm supports 30c, upon which respective actuator arms 32 are supported for pivoting movement relative to the housing 30. In the illustrated embodiment, each of the actuator arm supports 30c is a generally cylindrical protrusion that extends inwardly within the housing 30. However, the actuator arm supports 30c may have any desired shape or combination of shapes. Each of the illustrated actuator arms 32 is provided with a pair of legs 32a that define a pocket. The actuator arm supports 30c of the actuator arms 32 are respectively received within the pockets defined by the pairs of legs 32a of the actuator arms 32. Thus, as will be explained in detail below, the actuator arms 32 are respectively supported on the actuator arm supports 30c of the housing 30 for independent pivoting movement relative thereto.

The first ends of the actuator arms 32 are respectively disposed adjacent to the inner ends of the push buttons 31. The actuator arms 32 also include respective second ends that are disposed remotely from the first ends. In the illustrated embodiment, respective engagement pads 33 are secured to the inner surfaces of the second ends of the actuator arms 32. The engagement pads 33 may be formed from any desired material or combination of materials and may, if desired, be omitted entirely. However, it is preferred that the engagements pads 33 be formed from a material having a relatively high coefficient of friction, such as rubber. The purpose for the engagement pads 33 will be explained below.

Lastly, the housing 30 of the clamp 21 may include a pair of springs 34 that independently bias the two actuator arms 32 toward each other. In the illustrated embodiment, each of the springs 34 is formed from a flat piece of resilient material, such as a metallic material, that has been deformed to achieve a desired shape and bias. However, the springs 34 may be formed from any desired material or combination of materials and take any shape. The springs 34 may have first ends that are received within respective spring supports 30d provided on the inner surface of the housing 30. The springs 34 also may have second ends that bear inwardly upon respective outer surfaces of the second ends of the actuator arms 32. The purpose for the springs 34 will be explained below.

FIG. 4 illustrates the clamp 21 of the balloon catheter assembly 10 in a locked condition. In this locked condition, the second ends of the springs 34 bear inwardly upon respective outer surfaces of the second ends of the actuator arms 32. As a result, the engagements pads 33 are urged inwardly toward one another, as shown at 35, so as to engage and may exert a force on opposed portions of the outer surface of the outer member 11 of the balloon catheter assembly 10, which extends through the interior of the housing 30 of the clamp 21. As mentioned above, the engagements pads 33 are preferably formed from a material having a relatively high coefficient of friction. Thus, when the clamp 21 of the balloon catheter assembly 10 is in the locked condition, the outer member 11 of the balloon catheter assembly 10 is hindered or wholly prevented from moving axially relative to the housing 30 of the clamp 21. As mentioned above, the housing 30 of the clamp 21 is connected at the tip 30a to the sheath 22 for movement therewith. Accordingly, when the clamp 21 of the balloon catheter assembly 10 is in the locked condition, the outer member 11 of the balloon catheter assembly 10 is also prevented from moving axially relative to the sheath 22.

FIG. 5 illustrates the clamp 21 of the balloon catheter assembly 10 in an unlocked condition. To achieve this unlocked condition, a user of the balloon catheter assembly 10 may apply inwardly directed forces, as shown at 36, against the manually operable push buttons 31. These forces overcome the forces exerted by the springs 34 and cause the actuator arms 32 to pivot such that the engagements pads 33 are moved out of engagement, as shown at 37, with the opposed portions of the outer surface of the outer member 11 of the balloon catheter assembly 10. Thus, when the clamp 21 of the balloon catheter assembly 10 is in the unlocked condition, the outer member 11 of the balloon catheter assembly 10 is permitted to move axially relative to the housing 30 of the clamp 21. As mentioned above, as the housing 30 of the clamp 21 may be connected at the tip 30a to the sheath 22 for movement therewith, when the clamp 21 of the balloon catheter assembly 10 is in the unlocked condition, the outer member 11 of the balloon catheter assembly 10 is also permitted to move axially relative to the sheath 22.

Although this invention has been described in the context of the illustrated clamp 21, it will be appreciated that this invention may be practiced with any other desired structure for preventing the balloon 15 from slipping in relation to the sheath 22. For example, a variety of known structures may be used for this purpose. Some of such known structures include a duckbill pinch, a spring-activated clamp, a screw mechanism onto catheter, a Tuohy-Borst type of valve, and the like. Furthermore, it is possible to practice this invention without any clamp 21.

Figure 6:
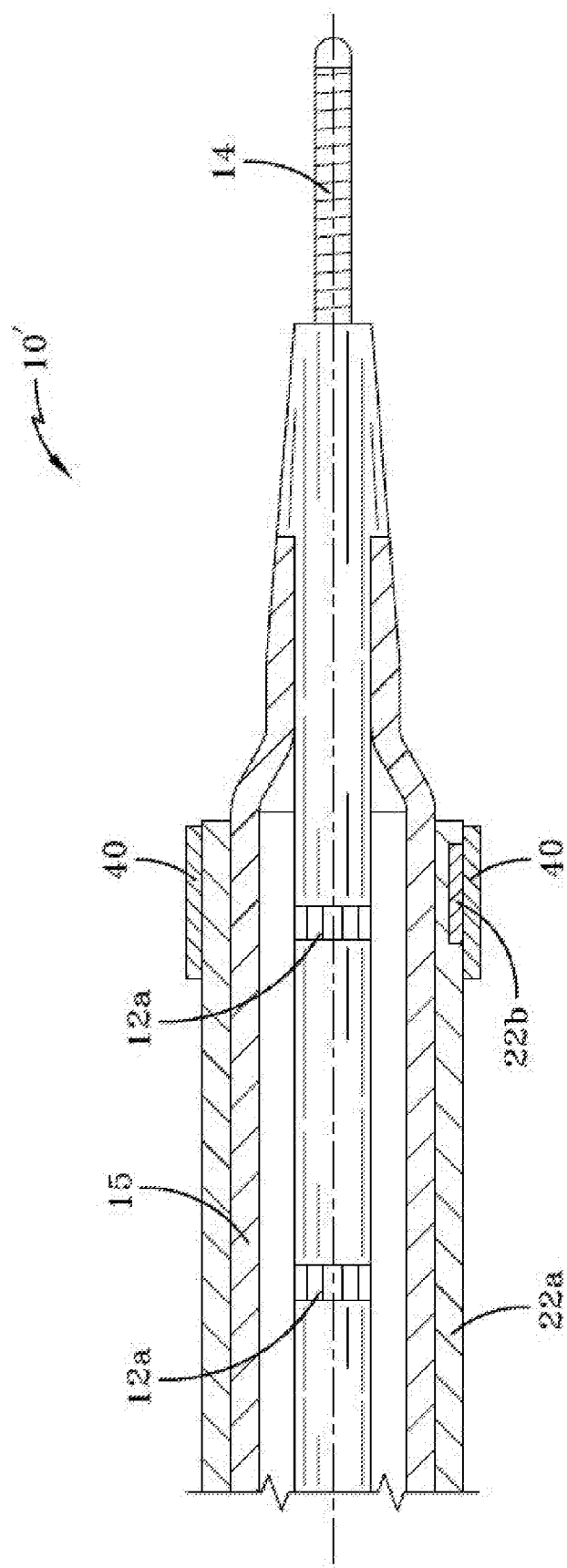
FIG. 6 is a further enlarged sectional elevation view of a second end of a balloon catheter assembly.

FIG. 6 illustrates a second end of the balloon catheter assembly, indicated generally at 10', in accordance with this invention. Like reference numbers are used to indicate components that are the same as described above. As shown therein, the second end of the modified balloon catheter assembly 10' has a collar 40 provided thereon. The purpose of the collar 40 is to prevent the sheath 22 from splitting or otherwise being deformed or damaged as a result of the pressure force exerted by the balloon 15 when it is inflated. The illustrated collar 40 is tubular in shape and extends completely about the end of the sheath 22 where the balloon 15 is located. However, it will be appreciated that the collar 40 may have any desired shape and may be located at any desired position on the sheath 22 or cover any desired portion of the sheath 22. The collar 40 may be formed from any desired material, such as a metallic material, a high strength aramid fiber material (such as is commercially available under the Kevlar® brand name), a high durometer plastic material, or the like. If desired, the collar 40 may be formed from a radiopaque material, allowing it to function as a marker for the distal tip of the sheath 22. If desired, the distal tip of the sheath 22 may be provided with a smooth edge (not shown) so as not of to present a sharp edge toward the balloon 15.

The tip of the balloon 15 may fit snugly into the end of the sheath 22 so as to provide a watertight engagement therebetween. Such a watertight engagement would maintain the integrity of the interior compartment of the balloon catheter assembly 10 during its insertion within a blood vessel or other portion of a body and during travel to the treatment site. This may be utilized to maintain a dry interior. Maintaining the interior compartment of the balloon catheter assembly 10 dry facilitates the use of conventional drug-coated balloons, stents, and other devices. The coatings provided on such devices are, in some instances, activated by contact with blood and water. In known catheter assemblies, a significant amount of the drugs provided on the balloons, stents, and other devices can be eluted during the initial insertion of the catheter assembly through blood vessels having flowing blood. The watertight engagement of this invention allows for minimal elution of the drugs during the initial insertion of the balloon catheter assembly 10 and maximal delivery of the drugs to the desired site. As will be explained in greater detail in subsequent figures, a sealed engagement may alternatively be obtained by the use of a tapered insertion tip 60. A lubricious coating may be provided between the sheath 22 and the outer surface of the balloon 15, such that the lubricious coating may reduce or eliminate disturbance to the drug coating when the balloon 15 is moved relative to the sheath 22.

Figure 7:
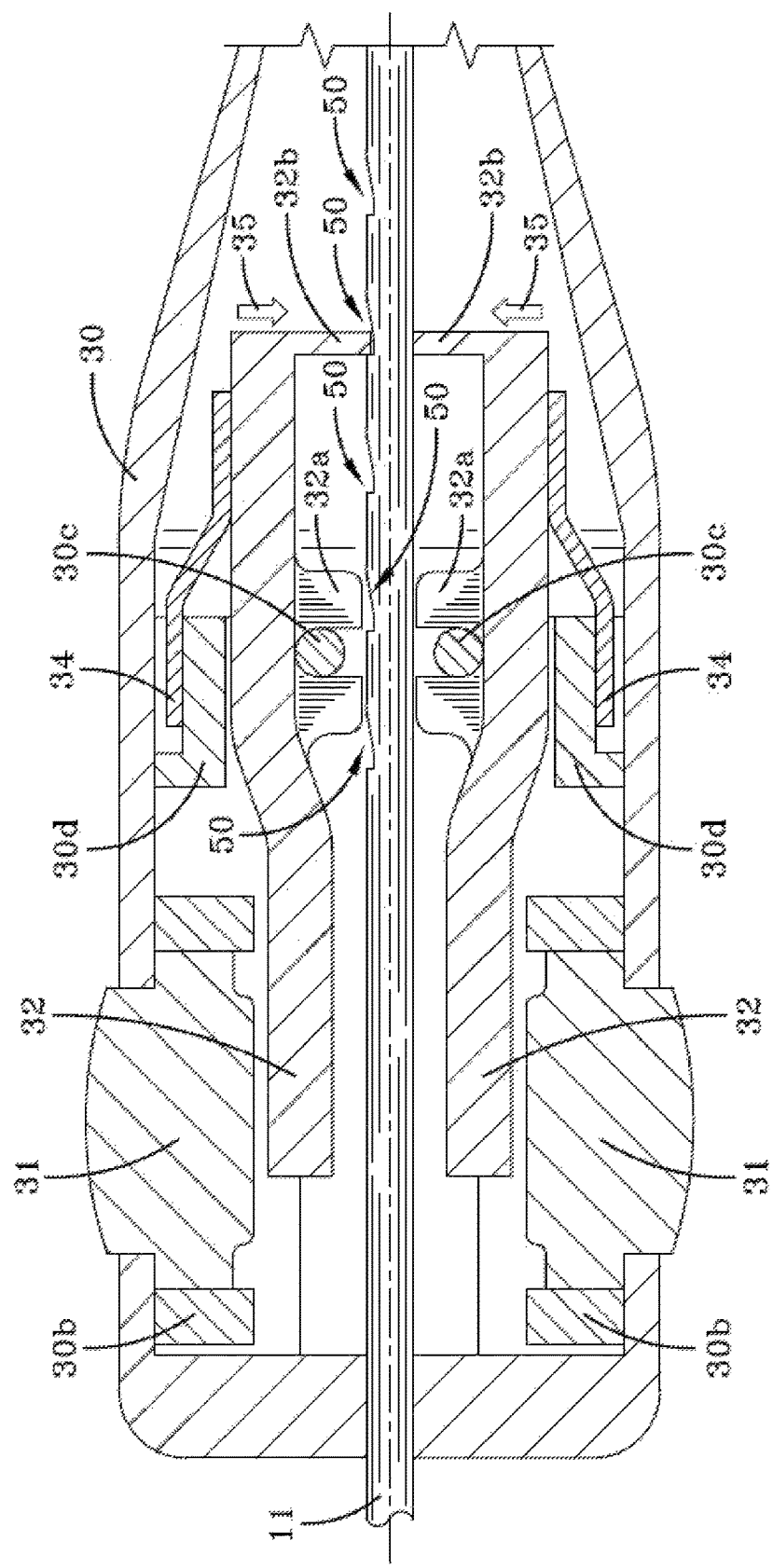
FIG. 7 is an enlarged sectional elevation view similar to FIG. 4, wherein a series of spaced indentations/protrusions are provided on one side of the movable sheath.

FIG. 7 illustrates one side of the outer member 11 provided with a plurality of spaced indentations or protrusions, indicated generally at 50. The indentations or protrusions 50 may have any desired shape or size (or combination of shapes and sizes) and may be provided at any desired location(s) on the one side of the outer member 11. Any number of indentations or protrusions 50 is contemplated.

The indentations or protrusions 50 are adapted to cooperate with one or more inwardly extending portions 32b provided on either or both of the actuator arms 32. Thus, when the clamp 21 of the balloon catheter assembly 10 is in the locked condition, the inwardly extending portions 32b provided on either or both of the actuator arms 32 engage one or more of the indentations or protrusions 50. As a result, the outer member 11 of the balloon catheter assembly 10 is prevented from moving axially relative to the housing 30 of the clamp 21. Conversely, when the clamp 21 of the balloon catheter assembly 10 is in the unlocked condition, the inwardly extending portions 32b provided on either or both of the actuator arms 32 do not engage one or more of the indentations or protrusions 50. As a result, the outer member 11 of the balloon catheter assembly 10 is permitted to move axially relative to the housing 30 of the clamp 21.

Figure 8:
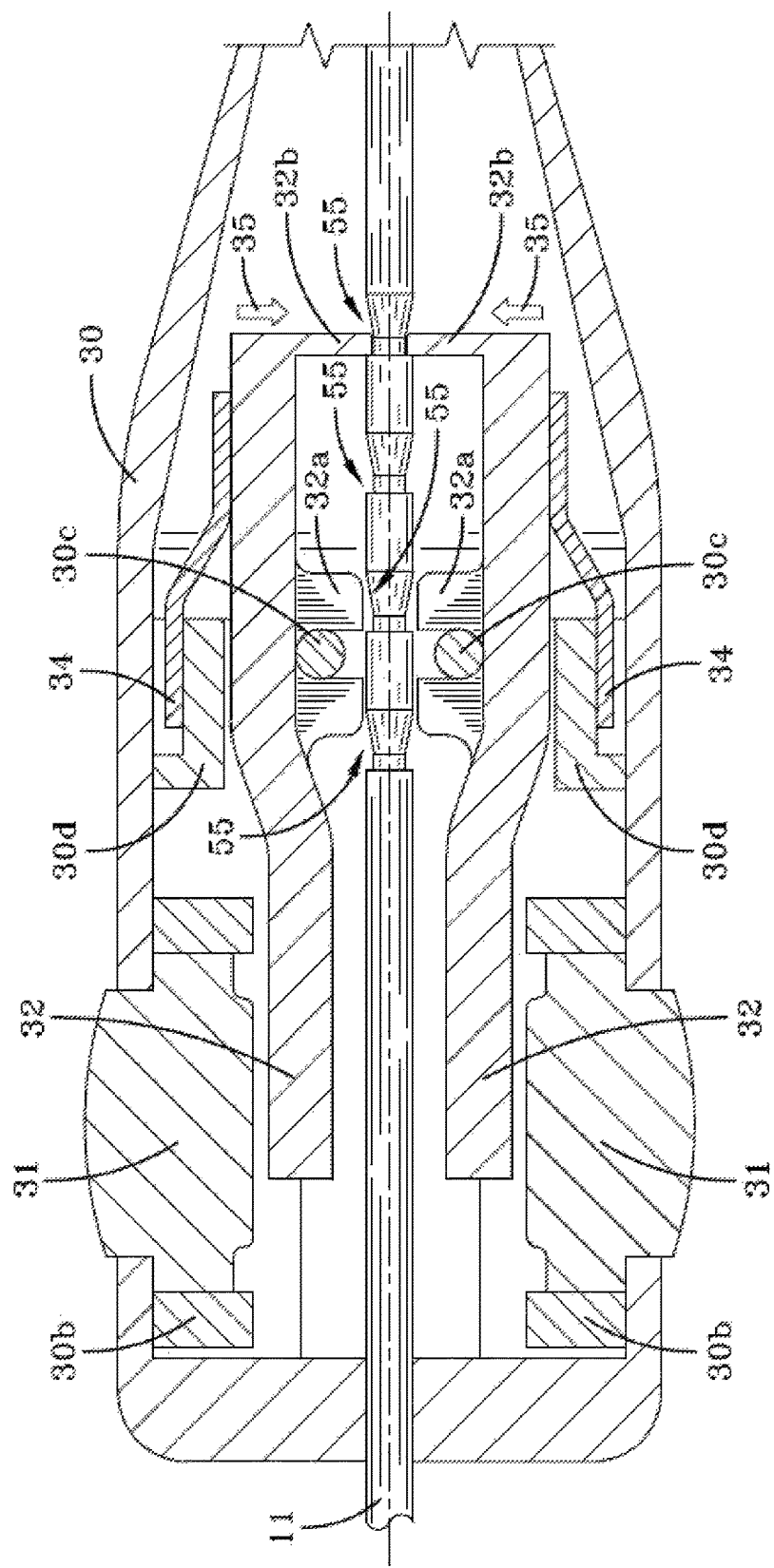
FIG. 8 is an enlarged sectional elevation view similar to FIG. 7, wherein a series of annular spaced indentations/protrusions are provided about the circumference of the movable sheath.

FIG. 8 illustrates a series of annular spaced indentations or protrusions, indicated generally at 55. The indentations or protrusions 55 may have any desired shape or size (or combination of shapes and sizes) and may be provided at any desired location(s) on the outer member 11. Any number of indentations or protrusions 55 is contemplated. The indentations or protrusions 55 are adapted to cooperate with one or more of the inwardly extending portions 32b provided on either or both of the actuator arms 32. Thus, when the clamp 21 of the balloon catheter assembly 10 is in the locked condition, the inwardly extending portions 32b provided on either or both of the actuator arms 32 engage one or more of the indentations or protrusions 55. As a result, the outer member 11 of the balloon catheter assembly 10 is prevented from moving axially relative to the housing 30 of the clamp 21. Conversely, when the clamp 21 of the balloon catheter assembly 10 is in the unlocked condition, the inwardly extending portions 32b provided on either or both of the actuator arms 32 do not engage one or more of the indentations or protrusions 55. As a result, the outer member 11 of the balloon catheter assembly 10 is permitted to move axially relative to the housing 30 of the clamp 21.

The annular spaced indentations or protrusions 55 may be a series of identical annular spaced indentations or protrusions 55. Each section of the annular spaced indentations or protrusions 55 may be defined by a tubular section with an outer diameter smaller than the outer diameter of the outer member 11, a conical section with an initial outer diameter equal to the smaller outer diameter of the previous section, transitioning to an outer diameter substantially equal to the outer diameter of the outer member 11, and finally, a second tubular section with an outer diameter substantially equal to the outer diameter of the outer member. This design allows for the inwardly extending portions 32b to ratchet as each section of the annular spaced indentation or protrusion 55 passes the inwardly extending portions 32b. This may provide the user with tactile and audible feedback as each section passes through the inwardly extending portion 32b. In the illustrated embodiment this would prevent the clamp 21 from moving distally relative to the balloon catheter assembly 10. It is contemplated that the annular spaced indentations or protrusions 55 may be reversed such that the indentations or protrusions 55 prevent the clamp 21 from moving proximally relative to the balloon catheter assembly 10.

Figure 9:
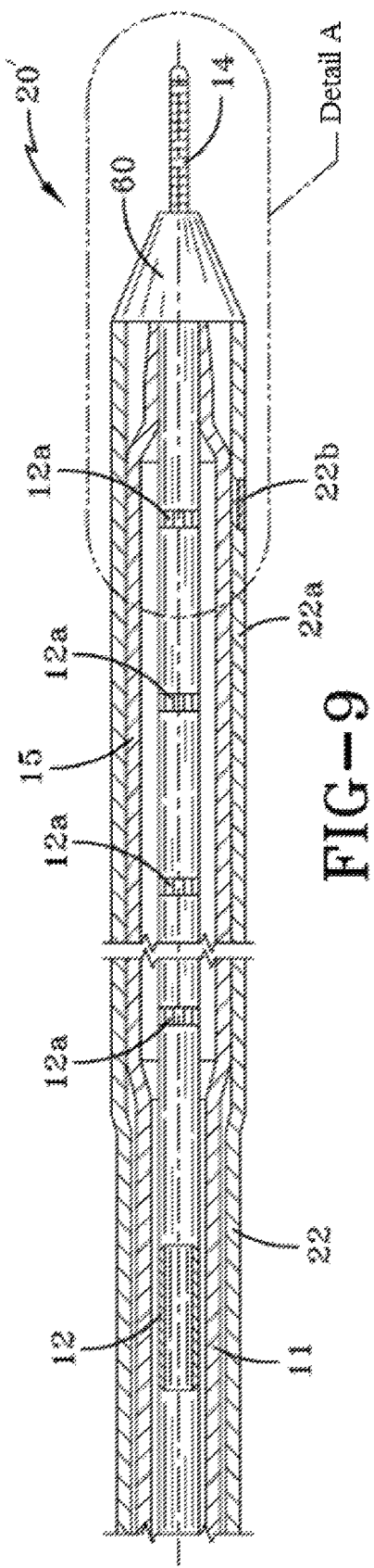
FIG. 9 is a sectional elevation view similar to FIG. 2 showing the end of the sheath hi sealing engagement with a tapered insertion tip and indicating Detail A.
Figure 10:
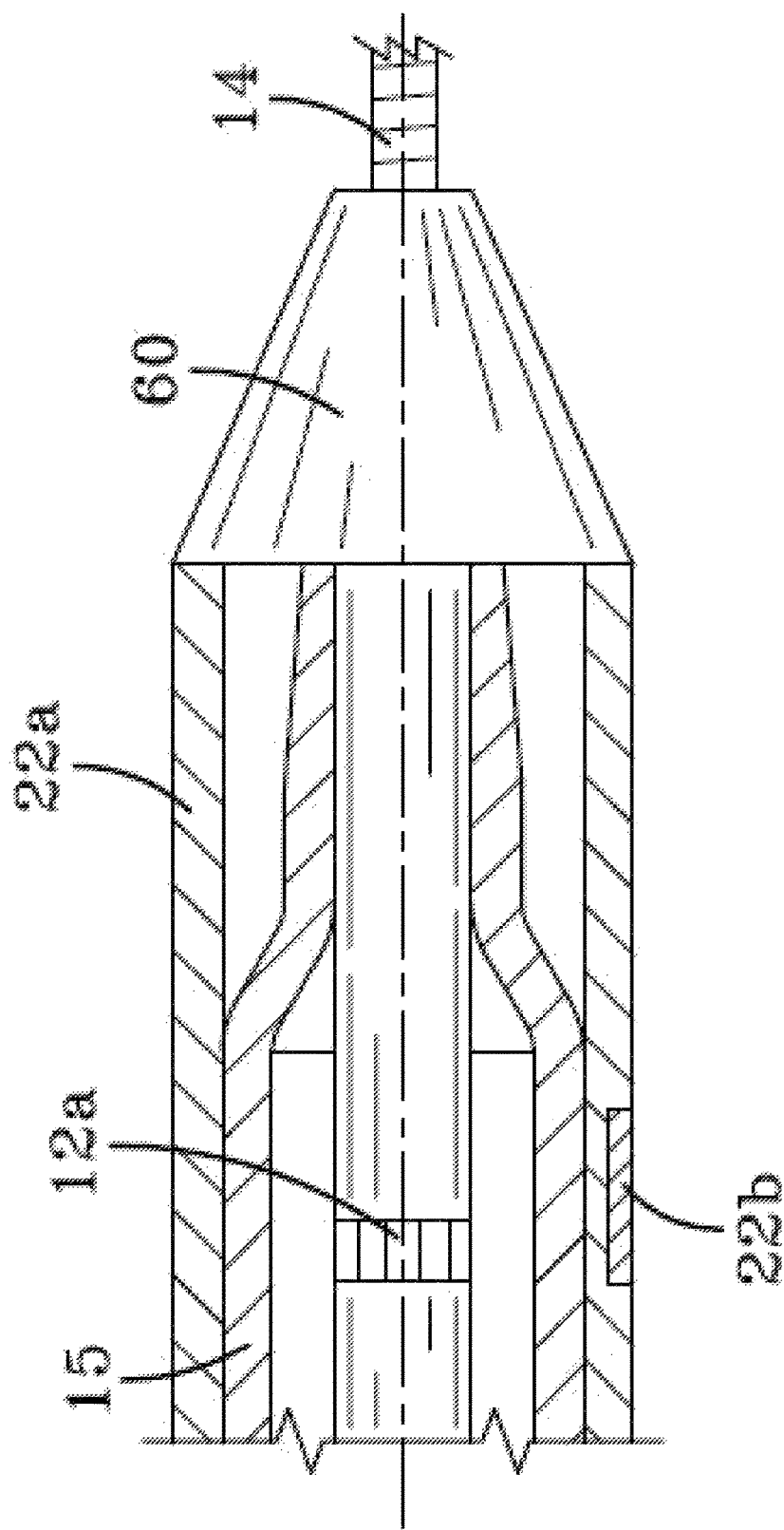
FIG. 10 is an enlarged view of the tapered insertion tip illustrated in Detail A of FIG. 9.
Figure 11:
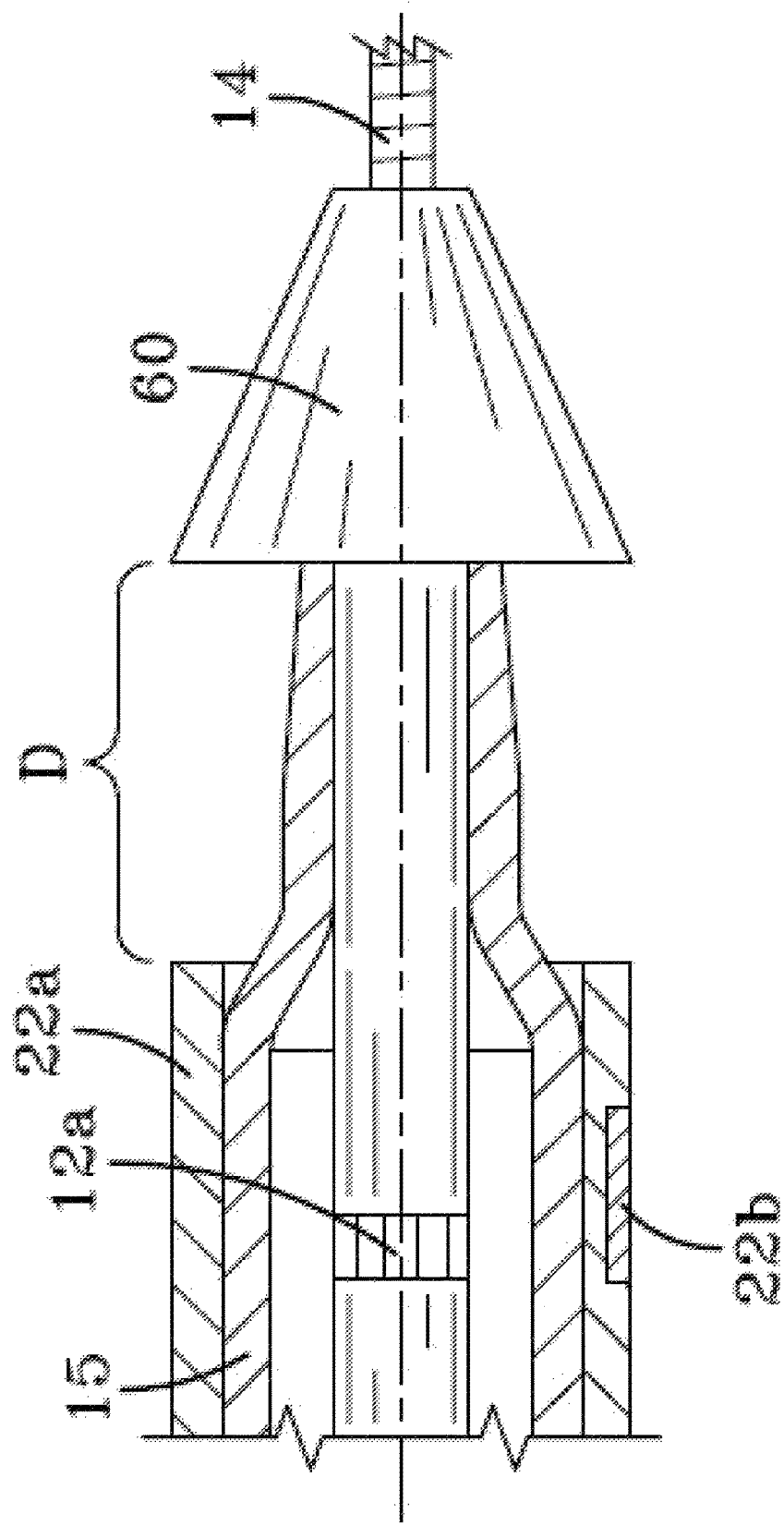
FIG. 11 is an enlarged view similar to FIG. 10 showing the sheath partially retracted to expose the balloon.

FIG. 9, FIG. 10, and FIG. 11 illustrate a modified end of the adjustable sheath assembly 20' with the tapered insertion tip 60. In FIG. 9 and FIG. 10, the end of the adjustable sheath assembly 20' is in sealing engagement with the tapered insertion tip 60. FIG. 11 is similar to FIG. 10, but shows the end of the adjustable sheath assembly 20' partially retracted to expose the balloon 15 in the manner described above. One or more radiopaque markers (not shown) may be placed on the tapered insertion tip 60 and monitored using conventional fluoroscopy techniques such that the user may determine the distance, shown in FIG. 11 as "D", between the sheath 22a and the tapered insertion tip 60. This also permits the user to determine the exposed length of the balloon 15.

The sheath 22 and tapered insertion tip 60 may protect the drug coating or drug coated devices such that the drug coating is not activated, eluted, diluted, or removed when the balloon catheter assembly 10 is placed into the blood vessel. In exemplary embodiments of the present invention, the balloon 15 alone may provide a sealing engagement with the sheath 22. The balloon catheter assembly 10 may additionally comprise a lubricious coating provided between the sheath 22 and the balloon 15 to facilitate the movement of the balloon 15 relative to the sheath 22 by reducing or eliminating disturbance to the drug coating. In exemplary embodiments of the present invention, the lubricious coating may additionally or alternatively be combined with or placed over the top of the medicated coating.

Figure 12:
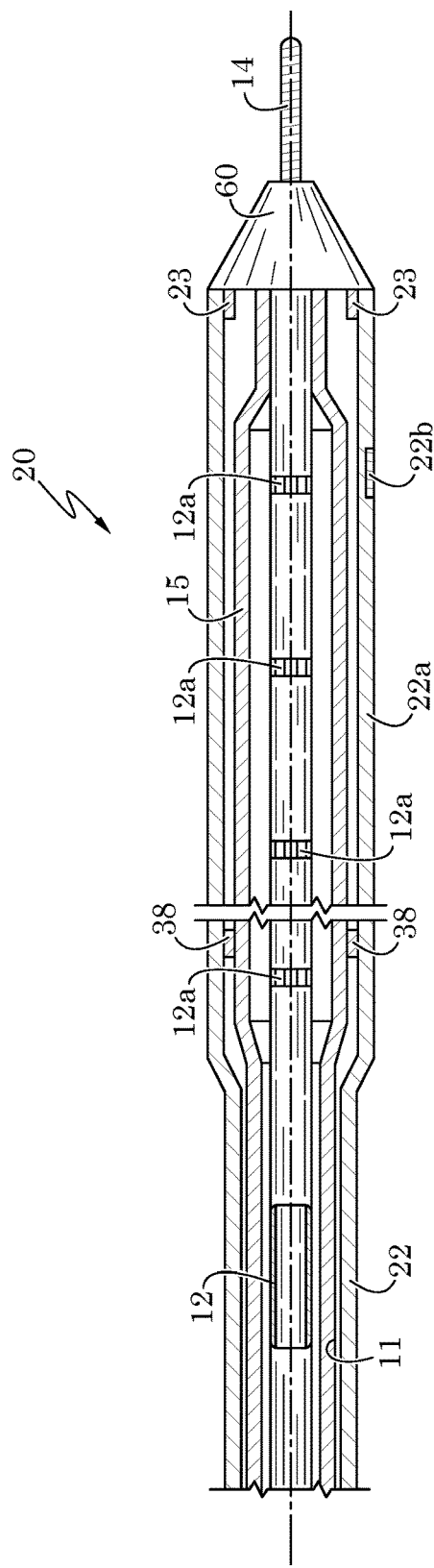
FIG. 12 is a sectional elevation view similar to FIG. 9 showing an exemplary embodiment of a mechanical stop.

FIG. 12 illustrates the adjustable sheath assembly 20 of the balloon catheter assembly 10, further comprising a mechanical stop. The mechanical stop may comprise an annulus 23 and a block 38. A sheath lumen may be defined as the opening between the outer surface of balloon 15 and the expanded portion 22a. In exemplary embodiments of the present invention, there may be no sheath lumen, as the sheath 22 substantially fits the curvature of the balloon 15. The annulus 23 may be located on the distal end of the expanded portion 22a. The annulus 23 may comprise an annual member located on the inner surface of the expanded portion 22a having a thickness such that it protrudes inwardly, thereby restricting the sheath lumen. The stop 38 may comprise a corresponding annual member 38 located on the outer diameter of the balloon 15, though any shape capable of frictionally engaging the annulus 23 is contemplated. The outer dimension of the stop 38 has an outer diameter larger that the lumen created by the annulus 23. In such an embodiment, the outer diameter of the corresponding stop 38 is configured such that it frictionally engages annulus 23, thereby preventing the balloon 15 from extending beyond the annulus 23.

Figure 13:
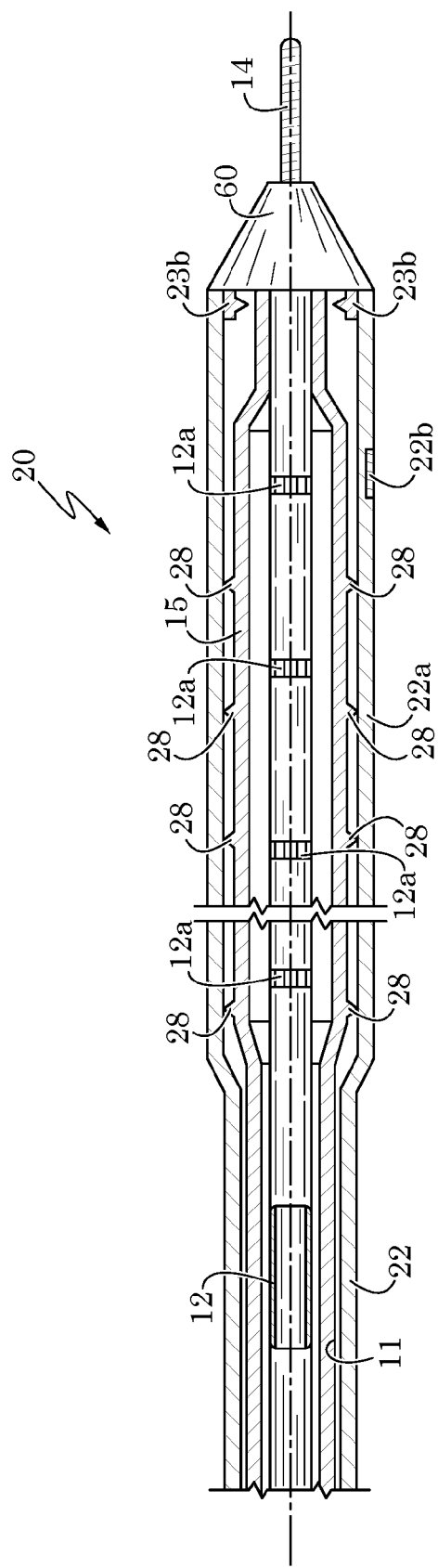
FIG. 13 is a sectional elevation view similar to FIG. 12 showing another exemplary embodiment of the mechanical stop.

FIG. 13 illustrates another exemplary embodiment of the present invention in which the assembly 10 further comprises one or more ridges 28 located on the outer surface of the balloon 15 that extend vertically therefrom. The mechanical stop may comprise an annular shaped pointed member 23b that it protrudes inwardly from the inner surface of the distal end of the expanded portion 22a, thereby restricting the sheath lumen, and the ridges 28. Further, the pointed shape of the pointed member 23b may be complementary to the shape of each of the ridges 28. As the balloon 15 is advanced relative to the sheath 22, the pointed member 23b may selectively secure the balloon 15 by frictionally engaging each of the ridges 28. In exemplary embodiments, the ridges 28 are formed as part of the balloon 15. Alternatively, the ridges 28 may be separately formed and attached to the outer diameter of balloon 15. Any number of ridges 28 is contemplated. Additionally, the ridges 28 may be equally spaced apart along balloon 15, though any spacing is contemplated. The series of ridges 28 may be comprised of a sufficiently rigid material such that each ridge 28 may not pass through the lumen created by the pointed member 23b without the user exerting a force on the assembly 10 such that the ridge 28 or the pointed member 23b may be sufficiently deformed to pass though the lumen created by pointed member 23b. This force may be exerted by the user directly on the outer member 11. Alternatively, this force may be exerted by the user on the outer member by use of the clamp 21.

Figure 14:
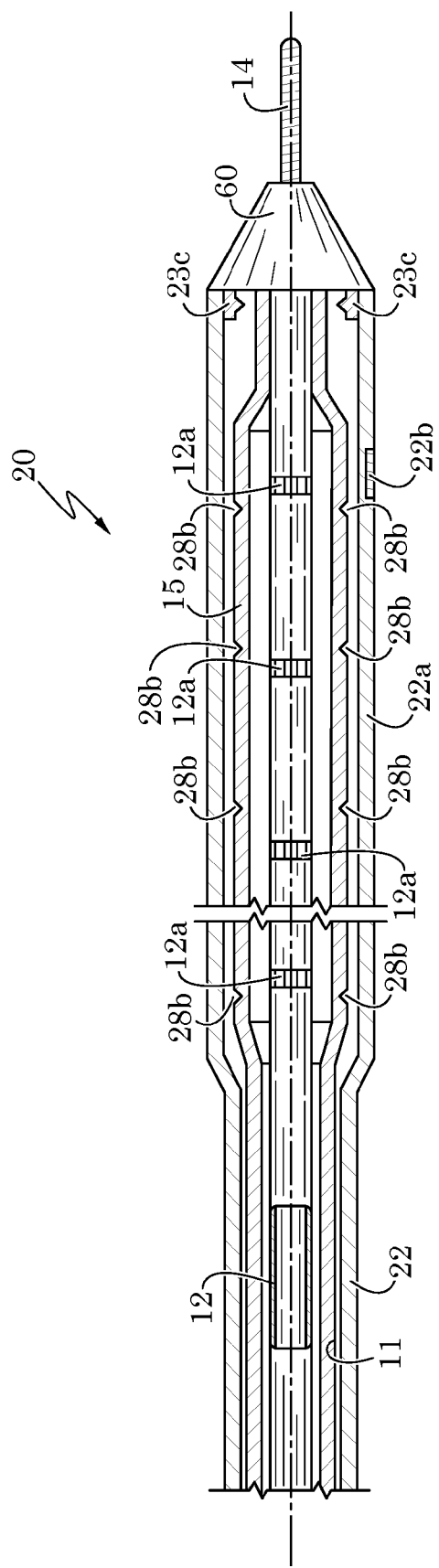
FIG. 14 is a sectional elevation view similar to FIG. 12 showing another exemplary embodiment of the mechanical stop.

FIG. 14 illustrates another exemplary embodiment wherein the balloon 15 comprises a series of valleys 28b located on the outer diameter of the balloon 15. The valleys 28b reduce the thickness of the balloon 15 such that outer diameter of the balloon 15 is reduced. Any number of valleys 28b is contemplated. Said valleys 28b may be equally spaced apart along the balloon 15, though any spacing is contemplated. A pointed member 23c may selectively secure movement of the balloon 15 relative to the sheath 22 by frictionally engaging each of the valleys 28b as they move through the lumen created by the pointed member 23c. The shape of the pointed member 23b may be formed complementary to the void created by each of the valleys 28b. The pointed member 23c may be comprised of a sufficiently flexible material such that each of the valleys 28b may not pass through the lumen created by the pointed member 23c until the user exerts force on the assembly such that the pointed member 23c or the balloon 15 is sufficiently deformed to permit each of the series of valleys 28b to pass through the lumen created by the pointed member 23c. This force may be exerted by the user directly on the outer member 11. Alternatively, this force may be exerted by the user on the outer member by use of the clamp 21.

Figure 15:
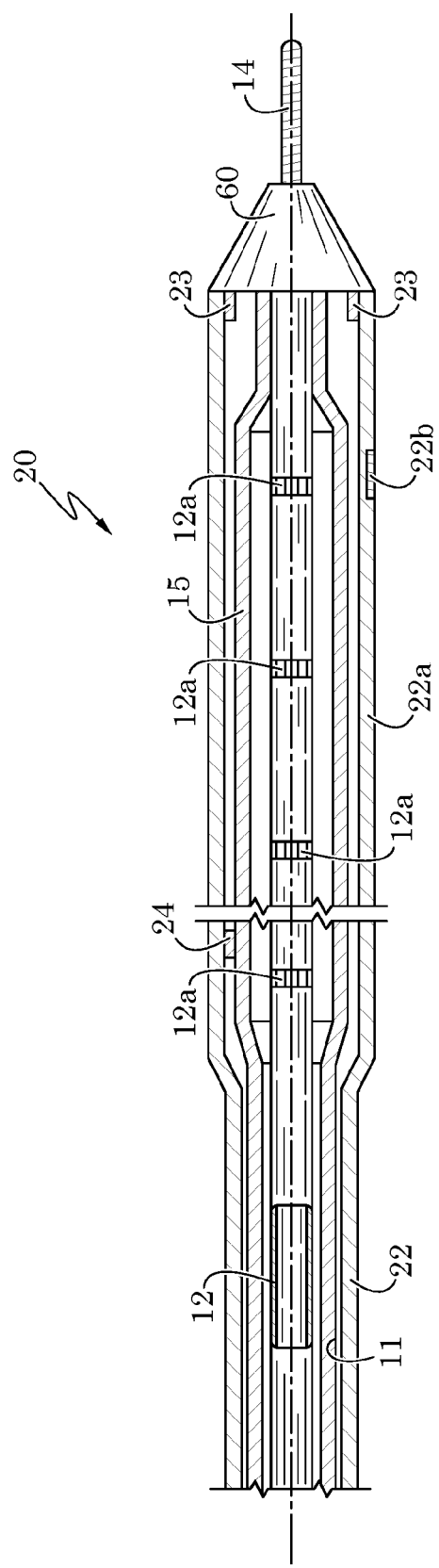
FIG. 15 is a sectional elevation view similar to FIG. 12 showing another exemplary embodiment of the mechanical stop.

FIG. 15 illustrates another exemplary embodiment of the present invention wherein the mechanical stop comprises a block 24, which may be attached to the balloon 15. The block 24 may be attached to the outer diameter of the balloon 15. The block 24 may be in the shape of a "T" such that the vertical section of the "T" extends vertically from the outer surface of balloon 15 and the horizontal portion of the "T" is curved and secured to the outer surface of the balloon 15, though any shape is contemplated. As the balloon 15 is extended from the expanded portion 22a, the block 24 frictionally engages the mechanical stop 23. In other exemplary embodiments of the present invention, the block of any shape may be used in place of the block 24.

Figure 16:
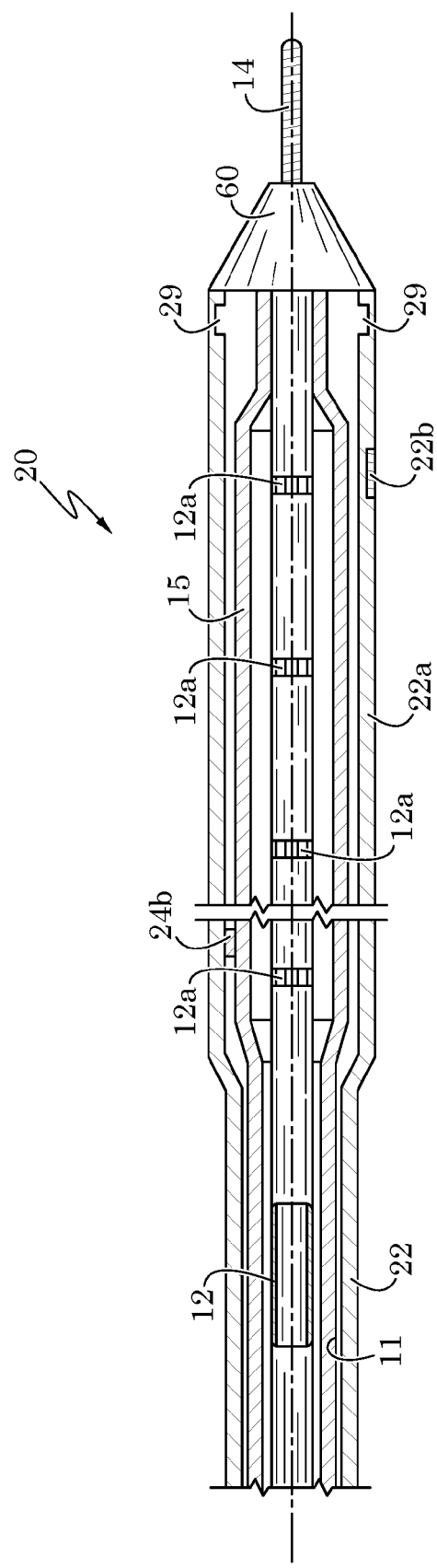
FIG. 16 is a sectional elevation view similar to FIG. 12 showing another exemplary embodiment of the mechanical stop.

FIG. 16 illustrates another exemplary embodiment of the mechanical stop comprising a circumferential slot 29 located on the inner surface of the expanded portion 22a. The slot 29 may be configured to accommodate and frictionally engage a collapsible block 24b such that as the balloon 15 is extended from the expanded portion 22a, the collapsible block 24b expands and enters the slot 29, thereby preventing the balloon 15 from further extending relative to the expanded portion 22a. In exemplary embodiments of the present invention, a collapsible orthotope, column, "T", or other shape collapsible device may be used. The collapsible block 24b, or the portion of the collapsible block 24b extending into the slot 29, may be spring loaded or otherwise biased into an expanded position.

Figure 17:
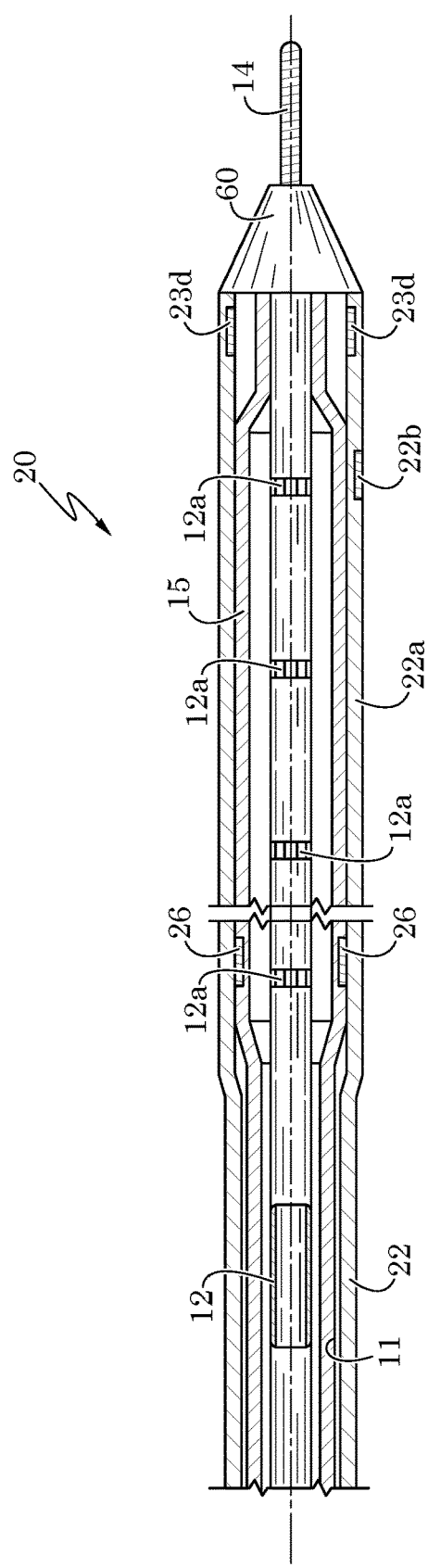
FIG. 17 is a sectional elevation view similar to FIG. 12 showing another exemplary embodiment of the mechanical stop.

FIG. 17 illustrates another exemplary embodiment in which the mechanical stop comprises a first and second portion 26 and 23d. The first and second portion 26 and 23d may be located on the outer surface of the balloon 15 and the inner surface of the sheath 22, respectively, and may comprise a surface or a coating with a relatively high coefficient of friction. The remainder of the balloon 15 and the sheath 22 may comprise a surface or a coating with a relatively low coefficient of friction such as a polymer, silicone, and/or further comprising a lubricant is contemplated. The first and second portions 26 and 23d may comprise a rubber, polymer, or the like. Further, the first and second portions 26 and 23d may be comprised of a surface texture to increase the coefficient of frictions such as bumps or the like is contemplated. The first portion 26 may be located towards the proximal end of the balloon 15 relative to the clamp 21, though any location is contemplated. The second portion 23d may be located towards the distal end of the sheath 22 relative to the clamp 21, though any location is contemplated. The balloon 15 may extend relative to the sheath 22 until the first portion 26 encounters and frictionally engages the second portion 23d, thereby preventing the balloon 15 from traveling beyond.

Those having skills in the art will realize that these embodiments are merely exemplary and that any device that may be utilized with the present invention to prevent a section of balloon 15 from extending from the sheath 22. As such, any shape or design of mechanical stop capable of preventing a portion of balloon 15 from escaping the sheath 22 is contemplated. Further, those skilled in the art will recognize that a combination of the aforementioned embodiments may be utilized.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

What is claimed is:

1. An intravascular balloon catheter device comprising:
    an inner member;
    an outer member disposed about the inner member and comprising a balloon, said balloon having a proximal end and a distal end, wherein the proximal end of the balloon is connected to the outer member and the distal end of the balloon is connected to the inner member;
    a sheath disposed about the outer member and adapted for movement relative to the balloon so as to selectively expose a second portion of the balloon for inflation;
    a clamp configured to selectively secure the sheath at a desired position relative to the balloon such that a first portion of the balloon remains located within the sheath; and
    a mechanical stop positioned and configured to prevent the balloon from fully escaping the sheath;
    wherein the mechanical stop comprises an annulus secured to the inner surface of the sheath and a stop attached to the outer surface of the balloon;
    wherein said stop and said annulus frictionally engage one another when the balloon is moved relative to the sheath;
    wherein the sheath is configured to prevent the first portion of the balloon from inflating to a diameter larger than the sheath.

2. The device of claim 1 wherein:
    the clamp includes a housing that is in communication with the sheath and through which the outer member extends.

3. The device of claim 2 wherein:

the clamp further comprises a first and second actuator arm that are supported within the housing and are selectively movable into engagement with the outer member.

4. The device of claim 3 wherein:

the outer member further comprises a plurality of spaced indentations; and the first and second actuator arms are configured to sequentially engage the plurality of spaced indentations.

5. The device of claim 4 wherein:

the first and second actuator arms are biased into engagement with the outer member.

6. The device of claim 1 further comprising:

a series of radiopaque marker bands located at select intervals on the inner member.

7. The device of claim 1 further comprising:

a collar provided about an end of the sheath adapted to provide structural rigidity to the sheath.

8. The device of claim 1 wherein:

the balloon fits snugly into the sheath so as to provide a substantially watertight engagement therebetween.

9. The device of claim 1 further comprising:

a tapered insertion tip disposed about an end of the outer member configured to provide a substantially watertight engagement between said tip and said sheath when said tip is abutted to said sheath.

10. The device of claim 1 further comprising:

a drug coating provided on the outer surface of the balloon.

11. The device of claim 10 further comprising:

a lubricious coating provided between the outer surface of the balloon and the inner surface of the sheath.

* * * * *